(12) United States Patent
Hare (10) Patent No.: US 7,858,570 B2
(45) Date of Patent: Dec. 28, 2010

(54) COMPOSITIONS AND METHODS FOR REMOVING URUSHIOL AND TREATING THE RESULTING SKIN CONDITION

(76) Inventor: William D. Hare, 3 Anderson La., Princeton, NJ (US) 08540

( * ) Notice: Subject to any disclaimer, the term of this patent is extended or adjusted under 35 U.S.C. 154(b) by 654 days.

(21) Appl. No.: 11/930,098

(22) Filed: Oct. 31, 2007

(65) Prior Publication Data

US 2008/0107742 A1     May 8, 2008

Related U.S. Application Data

(62) Division of application No. 10/906,491, filed on Feb. 23, 2005.

(60) Provisional application No. 60/547,038, filed on Feb. 24, 2004.

(51) Int. Cl.
    *A61K 8/00*     (2006.01)
    *A61K 8/18*     (2006.01)

(52) U.S. Cl. .................... 510/139; 424/401; 510/130

(58) Field of Classification Search ............ None
    See application file for complete search history.

(56) References Cited

U.S. PATENT DOCUMENTS

| | | | |
|---|---|---|---|
| 4,199,575 A | 4/1980 | Gunther | |
| 4,259,318 A | 3/1981 | Duhe et al. | |
| 4,428,965 A | 1/1984 | Elsohly et al. | |
| 4,594,239 A | 6/1986 | Pluim, Jr. | |
| 4,663,151 A | 5/1987 | Waali | |
| 4,668,419 A | 5/1987 | Mosema | |
| 4,861,584 A | 8/1989 | Powell et al. | |
| 5,443,847 A | 8/1995 | West | |
| 5,607,980 A | 3/1997 | McAtee et al. | |
| 5,643,572 A | 7/1997 | Byers | |
| 5,686,074 A * | 11/1997 | Stewart | 424/736 |
| 5,753,245 A | 5/1998 | Fowler et al. | |
| 5,767,109 A * | 6/1998 | Sanchez et al. | 514/58 |
| 5,811,111 A | 9/1998 | McAtee et al. | |
| 5,859,066 A | 1/1999 | Rosen | |
| 5,990,065 A | 11/1999 | Vinson et al. | |
| 6,022,565 A | 2/2000 | Albert | |
| 6,110,475 A | 8/2000 | Toma et al. | |
| 6,113,929 A | 9/2000 | Karl | |
| 6,423,746 B1 * | 7/2002 | Yarbrough et al. | 514/561 |
| 6,667,026 B1 | 12/2003 | Goldman et al. | |
| 7,001,622 B1 | 2/2006 | Berndt | |
| 7,008,963 B2 | 3/2006 | Yarbrough | |
| 7,025,972 B2 | 4/2006 | Beall | |
| 7,144,173 B2 | 12/2006 | Policicchio et al. | |
| 7,198,806 B2 | 4/2007 | Berndt | |
| 7,351,474 B2 * | 4/2008 | Etzrodt et al. | 428/407 |

\* cited by examiner

*Primary Examiner*—Robert A. Wax
*Assistant Examiner*—Melissa S Mercier
(74) *Attorney, Agent, or Firm*—William D. Hare; McNeely, Hare & War, LLP (57) ABSTRACT

The present application is directed to various compositions to treat the itching and conditions that result from contracting poison ivy, poison oak, and poison sumac, as well as other plant and substances that contain substances that lead to a skin reaction but that upon removal alleviate the symptoms of the condition. In particular, the compositions described herein are useful for removing urushiol after it has contacted the skin. The compositions include granules or other scrubbing means to reach the urushiol in the skin, a mixture of surfactants to form a complex with the urushiol, counter-irritants to provide a soothing sensation to the irritated skin, and other functional ingredients to provide additional benefits to the individual who has contacted urushiol.

20 Claims, 1 Drawing Sheet

Figure 1

COMPOSITIONS AND METHODS FOR REMOVING URUSHIOL AND TREATING THE RESULTING SKIN CONDITION

RELATED APPLICATIONS

This application is a divisional of and claims priority from U.S. patent application Ser. No. 10/906,491, filed on Feb. 23, 2005, claiming priority from U.S. Provisional Patent Application No. 60/547,038 filed on Feb. 24, 2004. The entirety of both applications are incorporated herein in their entirety by reference.

TECHNICAL FIELD OF THE INVENTION

The technical field of the invention relates to concepts, compositions, and methods for removing urushiol from the skin, after a reaction has occurred, to thereby eliminate the irritant and itching, and allow the skin to heal.

BACKGROUND OF THE INVENTION

Poison Ivy, Poison Oak and Other Plants that Contain Urushiol

Poison ivy (*Toxicodendron radicans*), poison oak (*Toxicodendron diversilobum*), poison sumac, and various other similar plants cause allergic contact dermatitis in people. These plants are variously found throughout the United States. A subspecies of poison ivy (*T. radicans*; ssp. *Divaricatum*) is native to southern Baja Calif. and Sonora, Mexico. Reports show that there are at least four native species of *Toxicodendron* in North America, including seven subspecies of poison ivy, and three species in Malaysia and China, including two subspecies of poison ivy, one in China and one in Japan.

Poison oak is a widespread deciduous shrub throughout the mountains and valleys of California, generally at elevations below 5,000 feet. In some locations it grows as a climbing vine with aerial (adventitious) roots that adhere to the trunks of oaks and sycamores. Poison oak also forms dense thickets in chaparral and coastal sage scrub, particularly in central and northern California. Poison oak regenerates readily after disturbances such as fire and the clearing of land. Rocky Mountain poison oak (*Toxicodendron rydbergii*) occurs in canyons throughout the Western United States and Canada. Because the two species of Western poison oak often exhibit a viney growth form, they are considered to be subspecies of Eastern poison ivy.

The pinnately trifoliate leaves typically have three or five leaflets, the terminal leaf being on a slender rachis (e.g., a stalk or petiolule). Eastern poison ivy often has a longer rachis and the leaflet margins tend to be less lobed and serrated (i.e., less "oak-like"). In the similar-appearing squaw bush (*Rhus trilobata*) the terminal leaflet is sessile (without a stalk). Like many members of the Sumac Family (Anacardiaceae) new foliage and autumn leaves often turn brilliant shades of pink and red due to anthocyanin pigments. In the Eastern United States poison ivy is often mistaken for another common native called Virginia creeper (*Parthenocissus quinquefolia*), which has a similar growth habit and attractive autumn foliage, but with five leaflets rather than three. Virginia creeper belongs to the grape family (Vitaceae) along with the common wild grape (*Vitis girdiana*).

In poison ivy, during the late spring loose clusters (panicles) of small greenish-white flowers are produced in the leaf axils. Functional male and female flowers are typically produced on separate plants (dioecious), or occasionally, unisexual and bisexual flowers may occur on the same plant (polygamous). Male flowers contain five stamens and a rudimentary pistil surrounded by five cream-colored petals and five sepals. Female flowers have a fertile pistil (gynoecium) and reduced, sterile stamens. During summer and fall, female plants produce small clusters of ivory-white fruits, each with a papery outer exocarp, a soft waxy mesocarp and a hard stony endocarp surrounding the seed. The fruits of related shrubs such as squaw bush, lemonadeberry (*Rhus integrifolia*) and sugar bush (*Rhus ovata*) are reddish with a sticky-pubescent exocarp. The old adage about poison oak and poison ivy is quite accurate: "Leaves of three, let it be; berries white, poisonous sight."

Freshly cut stems exude a sticky, terpene oleoresin that oxidizes and polymerizes into a shiny black lacquer resembling pruning sealer. The resinous sap is produced in resin canals of the stems, roots, leaves and flowers. Cross sections of poison oak stems show distinct concentric annual rings (ring-porous wood). Numerous resin canals appear as tiny black dots and are confined to the phloem layer just inside the bark. Dark resin canals (appearing as black striations) also occur in the waxy mesocarp of the fruits just beneath the papery skin. Abundant resin canals is one of the reasons poison oak and poison ivy are placed in the genus *Toxicodendron* rather than the older genus *Rhus*. *Toxicodendron* is also the updated generic name for poison sumac (*T. vernix*) and the Japanese lacquer tree (*T. vernicifluum*), the commercial source of natural lacquer. The resin canals also contain urushiol, the insidious allergen that gives poison oak its bad reputation. The name is derived from "urushi", Japanese name for lacquer made from the sap of the Japanese lacquer tree ("kiurushi" or "urushi ki").

In addition to poison oak, poison ivy and poison sumac, a number of other species in the Sumac Family contain urushiol mixtures. In Japan, dermatitis reactions have been reported from contact with lacquered objects (from Japanese lacquer tree) such as bar tops, rifle stocks and toilet seats. Dermatitis has also been reported in people handling mangoes (*Mangifera indica*), shells of cashew nuts (*Anacardium occidentale*), the Rengas tree (*Gluta renghas*), Burmese lacquer tree (*Melanorrhoea usitata*) and two attractive Caribbean shrubs, *Metopium toxiferum* and *Comocladia dodonaea*. The name Rengas actually refers to several genera of large Malaysian trees with resinous sap that blackens when exposed to the air. Urushiols also occur in the seeds of *Ginkgo biloba* (Ginkgoaceae) and in several genera of the Proteaceae.

Urushiol Oil, Structure and Transport

Urushiol is the broad term given to the substance in the sap of poison ivy (*Toxicodendron radicans*), poison oak (*Toxicodendron diversilobum*), poison sumac, and other plants that causes allergic contact dermatitis in people. Urushiol is a clear, sticky oil, causes an allergic reaction, and is potent even on dead or dried plants, which causes urushiol to be hazardous even during the winter months. Some reports estimate that between approximately 50% and 70% of the U.S. population is allergic to urushiol. In fact, there is some clinical evidence shows that no one is completely immune to the urushiol but that the sensitivity is a matter of degree: some people are sensitive to small amounts while others react only to large amounts. Poison oak and poison ivy account for an estimated ten percent of lost work time in the U.S. Forest Service. In fact, hundreds of fire fighters who battle summer and fall blazes in California's coastal ranges are so severely affected that they are unable to work. People who breathe in the smoke and soot may develop serious inflammation of respiratory mucous membranes. Because of the serious economic impact due to lost employment time, poison oak "injuries" are covered by Workers' Compensation Insurance in California. It is reported that the monetary cost of this affliction is approximately one percent of the state's workers' compensation budget.

Reports indicate that urushiol is actually a mixture of phenolic compounds that are known as catechols, which are potent benzene ring compounds having a long side-chain of 15 or 17 carbon atoms. The side chain may be saturated or unsaturated with one, two, or three double bonds. It is reported that the immune reaction and specificity of the catechol molecule is determined by the long side-chain. Poison oak urushiol contains mostly catechols with 17 carbon side-chains (heptadecylcatechols), while poison ivy and poison sumac contain mostly 15 carbon side-chains (pentadecylcatechols). These compounds are illustrated below. Formula I depicts the chemical structure of urushiol in which there are five possibilities for the variable R:

Formula I $R=(CH_2KH_3)$  I

$R=HC=CH(CH_2)_5CH_3$  II $R=HC=CHCH_2CH=CH(CH_2)_2CH_3$  III $R=HC=CHCH_2CH=CHCH=CHCH_3$  IV $R=HC=CHCH_2CH=CHCH_2CH=CH_2$  V

Formula II depicts the chemical structure of the pentadecylcatechols in which there are four possibilities for the variable R:

Formula II $R=C_{15}H_{31}, C_{15}H_{29}, C_{15}H_{27}$ and $C_{15}H_{25}$

Formula III depicts the chemical structure of the heptadecylcatechols in which there are four possibilities for the variable R:

Formula III $R'=C_{17}H_{35}, C_{17}H_{33}, C_{17}H_{31}$ and $C_{17}H_{29}$

The above figures illustrate the chemical structure of urushiols found in resin canals of poison oak and poison ivy. Poison ivy mostly contains a mixture of four saturated pentadecylcatechols (with 15-carbon side chain), while poison oak contains a mixture of four heptadecylcatechols (with 17-carbon side chain).

As indicated above, the side chain may be saturated or unsaturated with one, two, or three double bonds. According to some studies, the immune reaction and specificity of the catechol molecule is a function of the long side-chain. As might be expected, the urushiol can vary based on the plant in which it is found. For example, the urushiol from poison oak contains mostly catechols with 17-carbon side-chains (heptadecylcatechols). In contrast, the urushiol from poison ivy and poison sumac contain mostly 15 carbon side-chains (pentadecylcatechols).

It has been reported that urushiol is found in only the resin canals of the plant and that it will be found on the plant's outer surfaces only if the leaves and stems are bruised or attacked by chewing/sucking insects such that it can reach the outer surface. Although nonvolatile, it may be carried in ash and dust particles and as minute droplets in smoke from burning foliage. Many surprised people and firefighters have learned to their detriment that although urushiol is nonvolatile, it is carried in ash and dust particles and as minute droplets in smoke from burning foliage. Thus, carefully clearing poison ivy and other urushiol-containing plants with diligence to avoid contact, but then burning them creates a urushiol-containing smoke that disperses the urushiol over a great area, including the eyes and lungs. Firefighters regularly encounter this hazard when fighting forest fires.

The Body's Reaction to Urushiol

Urushiol causes an irritating skin reaction on many people. The body's immune system treats urushiol as foreign and attacks the complex of urushiol-derivatives with skin proteins. In the absence of the immune attack, urushiol would be harmless. The reaction, an itchy rash with clear blisters, is variable in severity among people, and can vary from year to year on the same individual. Once the skin has been exposed to urushiol it is only a matter of hours, usually 24 to 72, before rash breaks out. Any area that comes into contact with the oil will react, except the mucous membranes, such as lips, mouth, and inside of the nose. The rash, *Rhus dermatitis*, starts off as red, swollen patches, with a few small fluid-filled blisters. As the reaction intensifies, the blisters become larger, and then break down and weep. The whole area becomes covered with an oozing, scaling crust. Contrary to popular belief, the rash itself does not "spread" like an infection. It is the unknowing transfer of the oil to other parts of the body by touching that gives the spreading affect. Once the oil is completely removed from skin and clothing, no further rash will result. Some rashes will appear sooner than others depending on the sensitivity of the skin area and the amount of urushiol contacted.

The poison ivy reaction can be reduced by changing clothing immediately after contact and washing the exposed skin with soap and water. It is reported that if a person can wash all the oil off exposed skin within 5 minutes of contact, no reaction will occur. Even water from a running stream can be an effective cleanser. Some people are so sensitive to urushiol that it only takes a molecular trace of urushiol (two micrograms or less than one millionth of an ounce) on the skin to initiate an allergic reaction. Even the amount on a surface the size of pinhead is sufficient to cause rashes in 500 sensitive people. Approximately 80-90 percent of adult Americans will get a rash if they are exposed to 50 micrograms of purified urushiol, which is a minute amount when considering that one grain of table salt weighs about 60 micrograms. An urushiol residue on the skin is difficult to wash off and may be spread by scratching. Contrary to popular belief, it is not spread through blister fluids. It is a relatively stable compound and can retain its potency for years in the absence of oxidation—herbarium specimens 100 years old have been known to cause dermatitis. Urushiol is readily transferred from contaminated clothing, objects and fur of animals. Moreover, it readily penetrates the epidermal layer of the skin where it binds to proteins of deeper skin cell membranes. Before the protein bond can occur the catechol (Formula IV) is oxidized to a more reactive quinone (Formula V) in which the two OH groups are replaced by double-bonded oxygens, as illustrated in the reaction schematic FIGURE below.

Formula IV         Formula V

The above illustration shows the chemical structure of poison oak urushiol (heptadecylcatechol) and its oxidized "reactive" quinone. The reactive quinone bonds to white blood cell membranes deep in the skin.

In the conjugated state (bound to cell membranes) urushiol is virtually impossible to wash off. By itself the urushiol molecule (also called a hapten) probably would not initiate a full-blown immune response, but when attached to the cell membrane it becomes a "warning flag" that attracts patrolling T-cells.

Figure 1:
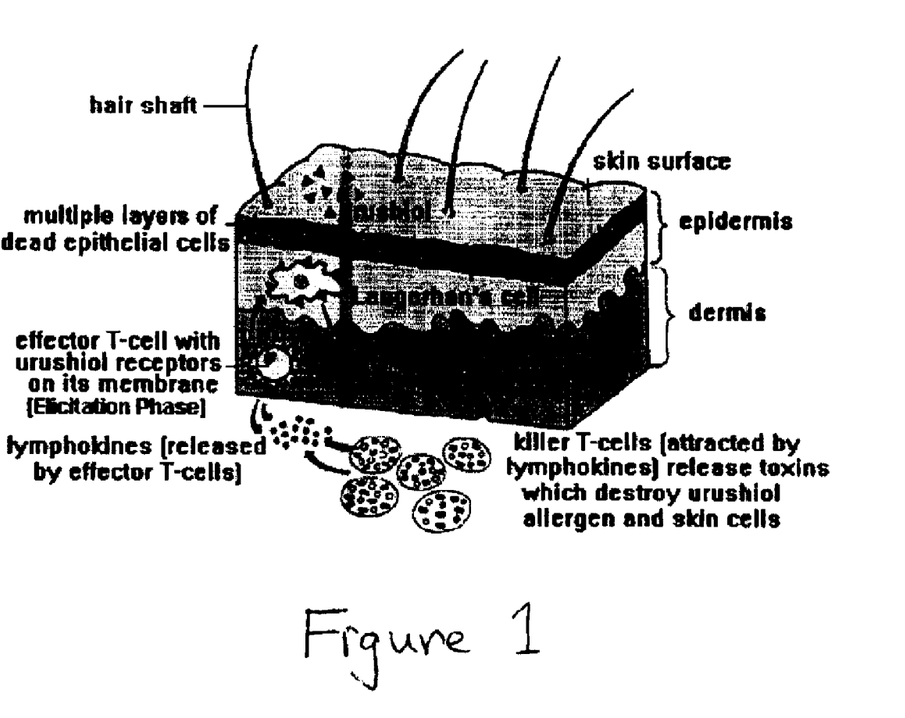
FIG. 1 is a perspective view of skin undergoing a reaction with urushiol.

Poison oak urushiol causes a complicated delayed allergic reaction with the body's immune system. It is technically classified as a cell-mediated immune response and the "peak misery" may not appear until days or weeks later. It is quite different from the primary irritants of nettle and euphorbias, the effects of which are immediate. The following hypothetical "two-phase" scenario for poison oak dermatitis is summarized from the scientific literature. PHASE I (Induction): Initial contact with poison oak may result in urushiol penetrating the stratified squamous epithelial cells of the skin and binding to large dendritic (branched) white blood cells in the epidermis called Langerhan's cells, as illustrated in FIG. 1, which illustrates a hypothetical mechanism for the poison oak scenario: a delayed action, cell-mediated immune response.

The Langerhan's cell (with urushiol allergen and MHC protein on its membrane) migrates to a nearby lymph node where clones of special white blood cells, called effector T-cells, are programmed to recognize urushiol. Some immunology textbooks refer to these clones of T-cells, with urushiol receptor sites on their membranes, as "helper T-cells." There are literally millions of effector T-cells (helper T-cells) roaming throughout the blood and lymphatic system, each with special receptor molecules on their membranes for a particular allergenic chemical, such as the urushiol of poison oak. T-cells patrol the body's circulatory system looking for invading cells and viruses.

PHASE II (Elicitation): Once urushiol is absorbed into the skin during a subsequent encounter with poison oak, an effector T-cell may encounter it bound to a Langerhan's cell and attach to it by a specific recognition system. The effector T-cell then produces more clones of itself and releases special proteins called lymphokines (cytokines) which attract a legion of different white blood cells, including "cell engulfing" macrophages and cytotoxic ("killer") T-cells. The killer T-cells are also produced in regional lymph nodes during the Elicitation phase, and according to some textbooks, they also have urushiol receptors on their membranes. The new army of white blood cells releases lytic enzymes and protein toxins (perforins) which destroy everything in the vicinity including membrane-bound urushiol and other skin cells, thus producing a blistering rash. Fluid oozes from the blood vessels and lymphatics (edema) and cell death and necrosis (breakdown) of skin tissue occurs. Milder effects range from redness (vasodilation) and itching (nerve injury) to small blisters (vesicles and bullae).

There is some natural immunity to poison oak. Sensitization depends on the chance meeting of a special effector T-cell (with correct receptor site) and the poison oak allergen—a painful biochemical rendezvous. A person may not have effector T-cells with the special receptor for urushiol—or perhaps a person that has relatively few effector T-cells with precise poison oak receptor may never encounter the urushiol allergen. The allergen may be absorbed and degraded before the T-cells find it. Immunity to poison oak with age, exposure and homeopathic remedies may involve suppressor T-cells which inhibit or block the action and reproduction of other T-cells. Circulating IgG immunoglobulin antibodies that block the T-cell receptor for urushiol may also be involved.

Since the HIV virus attacks helper T-cells, persons afflicted with the deadly disease AIDS have a serious deficiency in cellular (T-cell) immunity. AIDS patients may not have problems with poison oak dermatitis and this likely reflects their decreased cellular immunity. In fact, one treatment for AIDS patients is to try to sensitize them to another allergenic chemical (dinitrochlorobenzene) in order to stimulate T-cell production.

Treatments for Urushiol-Induced Contact Dermatitis

Scientists have tried many homeopathic remedies made from extracts of poison oak. Some products, such as poison oak tablets and droplets, were withdrawn from the market because of severe allergic reactions in hypersensitive people. One area of desensitization research involves oral pills and intramuscular injections of related or modified urushiol: A molecule similar enough to urushiol to have the same immunological effect, but different enough to avert its excruciating side effects. Other research may lead to a vaccine that blocks the specific urushiol T-cell receptor and immunizes "high risk" people against urushiol for periods of time. In fact, Allergene, a biotech company in San Mateo, Calif. has successfully produced a hybridoma (fused lymphocyte and carcinoma cell) that makes urushiol-binding monoclonal antibodies. These antibodies prevented sensitized mice from reacting with urushiol.

The complete list of topical treatments for poison oak and poison ivy includes an array of materials, including bleach, morphine, kerosene, buttermilk, and gunpowder. Lotions, creams and sprays containing anti-inflammatory corticosteroids (hydrocortisones) are generally accepted as being potential effective agents to relieve painful, itching rashes. Serious outbreaks may require medical attention and hospitalization. The ideal therapy when exposed to poison oak or ivy is to wash the contaminated areas thoroughly, unfortunately most ordinary bath soaps have little effect on removing the resinous sap. There are some reports that soaps with added moisturizers and oils together with brisk rubbing may even spread the urushiol, thereby increasing the area of allergic response. Strong laundry soaps, such as Fels Naptha, may also spread the allergen and be harsh on sensitive skin. Some sources recommend antipruritic (anti-itch) agents such as calamine lotion for mild cases.

Another remedy for the discomfort of itching poison oak and ivy lesions is a "pore minimizer" acne treatment with 2% salicylic acid (available from several manufacturers, including Neutrogena® and Johnson & Johnson). A poultice made from the resinous flowers and leaves of gum plant (*Grindelia robusta*) was commonly used by Indians and early settlers in California to relieve inflammation and itching. Native Americans also made concentrated poultices from boiled leaves of the common shrubs yerba santa and manzanita (*Eriodictyon* and *Arctostaphylos* spp.), and from the thick roots of mule ears (*Wyethia longicaulis*), a resinous, balsam-scented sunflower with large basal leaves. Other reported naturopathic remedies to relieve the inflammation and itching of poison oak rashes include salves made from the crushed leaves of *Aloe vera* and narrow-leaf plantain (*Plantago lanceolata*). Some herbal manuals list a poultice made from juicy stems of the North American jewelweeds (*Impatiens capensis* and *I. pallida*), succulent wildflowers that grow with poison ivy in the Eastern states; although its efficacy is questionable and possibly amply disproved.

A recent editorial in Mushroom The Journal (Winter 1994-95) discussed a mycological cure for poison oak rash by rubbing fungi such as *Boletus* and Polyporus on the affected skin. This treatment is based on the fact that freshly cut pieces of mushrooms, apples and potatoes turn dark when exposed to the air. The actual mechanism for this blackening process involves the oxidation of phenolic compounds in the tissues of these pieces by the enzyme tyrosinase. The resulting quinones rapidly polymerize into a brown residue. Placing the pieces under water prevents this "unsightly" oxidation. In fact, chefs add lemon juice, which contains the strong reducing agent ascorbic acid; this keeps the phenolics reduced. Since urushiol is a phenolic compound, tyrosinase would probably also detoxify it. The enzymes might also reduce the spreading of urushiol to other parts of the body by deactivating it at the initial site of exposure.

There is a report that an even more specific and potent oxidase for urushiol, catechol 2,3 oxidase, oxidizes the ring structure between carbon atoms # 2 and # 3 and thereby destroying the molecule. In the study, a bacterial gene was cloned and expressed to produce this recombinant enzyme, which oxidized the urushiol in vitro within seconds. The report further notes that when applied to skin the enzyme sometimes prevented a rash, but only if the urushiol was inactivated before penetrating the epidermis. The efficacy of patented creams containing oxidase enzymes depends on the oxidation of urushiol at the initial site of contact before it has penetrated the skin. Once urushiol binds to the protein of skin cell membranes, these creams would have little effect on the subsequent immune response.

There are a number of commercially available products. One product, called Tecnu Oak-n-Ivy® Cleanser, is now marketed through forestry supply catalogs. Tecnu is a crude distillate of gasoline and contains a mixture of organic solvents and wood pulp by-products which remove terpene resins and urushiol from the skin. Thorough rinsing with water is recommended. Similarly, other organic solvents, including rubbing alcohol, likely would remove the urushiol residue. However, if the allergen has already penetrated the epidermal layer and bonded to deeper skin cells it is too late. Another product that claims to remove urushiol from the skin, even after a rash has developed, is called Zanfel™. Yet another product developed for the U.S. Forest Service is called Ivy Block®. It is in the form of an aerosol spray or lotion containing activated bentonite clay used in antiperspirants. Ivy Block® is described as forming a barrier that both prevents urushiol from touching the skin and chemically binds with it so it becomes inactive. Another blocking agent, called StokoGard Outdoor Cream®, is a fatty acid ester and is available through industrial supply houses and through pharmacist who can order it from Stockhausen, Inc. of Greensboro, N.C.

A number of background sources on poison ivy include: waynesword.palomar.edu/ww0802.htm, chemweb.calpoly.edu/chel'n/bailey/377/PapersF2000/Dana/, and Dana Longinetti, Chem 377-Drugs and Poisons, Fall 2000.

SUMMARY OF THE INVENTION

In one general aspect there is provided a composition for applying to skin that has been in contact with urushiol. The composition includes a first compound, a second compound, and one or more counterirritants. The first compound has a group containing one or both of a carbon chain of less than nine carbon atoms or more than nine carbon atoms (one or more phenol ethoxylates having a carbon chain of less than nine carbon atoms or more than nine carbon atoms). The second compound has a group containing one or both of a carbon chain of less than eleven carbon atoms or more than eleven carbon atoms (one or more sodium sarcosinates having a carbon chain of less than eleven carbon atoms or more than eleven carbon atoms).

Embodiments of the composition may include one or more of the following features. For example, the one or more phenol ethoxylates may further include a carbon chain of less than nine carbon atoms. The one or more counterirritants may include one or more of the counterirritants described herein. The composition may further include one or more granular materials. The composition may further include one or more of a topical anesthetic, an antifungal agent, an antibiotic agent, and an antiviral agent. The composition may further include one or more granular means. The granular material or means may be one or more of granules, beads, microspheres, grit, and pumice. The granular material may be one or more of a polymer, sand, glass, and jojoba beads. The polymer may be one or more of a polyethylene, a polypropylene, and a polystyrene. The granular means may be porous. The granular means may be a pad, cloth or other scrubbing means.

In another general aspect there is provided a composition for applying to skin that has been in contact with urushiol. The composition includes one or more nonionic surfactants; one or more anionic surfactants; and a counter irritant. The surfactants are selected such that the form a complex with urushiol such that it can be removed upon scrubbing and application of a fluid.

The details of one or more embodiments of the compositions are set forth in the accompanying drawings and the description below. Other features and advantages of the compositions will be apparent from the description, the drawings, and the claims.

DETAILED DESCRIPTION

General Composition. The invention relates to compositions and methods useful for removing urushiol from the skin, before or after a reaction to the urushiol has occurred, to thereby eliminate the irritant and itching, and allow the skin to heal. The invention also relates to processes for making the composition and the various forms in which the compositions can be made. In one implementation, a composition includes one or more nonionic surfactants, one or more anionic surfactants and, optionally, one or more counter irritants, granules or the like, fillers, preservatives, thickening agents, moisturizers, colorants, emulsifiers, wetting agents, detergents, and alkalinizing agents. The surfactants are selected such that they cover a ranges of sizes such that some or all of the surfactants will provide complexes with the urushiol, derivatives, and related compounds. The complexes then can be removed by washing with a fluid.

The compositions may also include one or more of a topical analgesic and anesthetic agents, an antibiotic agent, an antifungal agent, an antiviral agent, an astringent agent, and those agents approved by the US FDA for the treatment of poison ivy, poison oak and poison sumac, as described and defined herein below. The surfactants interact with the urushiol on the skin and when washed off of the skin remove the urushiol along with them. The counter-irritants provide a sensation on the skin that causes relief to the itching caused by the urushiol. The granules provide immediate relief to the itching and roughen the skin to allow the surfactants to bond or interact with the urushiol so that it can be removed upon washing. The topical analgesic and anesthetic agents provide some degree of longer term relief to the itching. The antibiotic, antifungal, and antiviral agents provide longer term prevention against infection.

Further, the compositions optionally may include one or more of the following depending on the desired physical form, intended use, marketing objective, or other purpose: alkalinizing agent, humectant, detergent, wetting agent, antibacterial agent, stabilizer, emulsifier, antifungal agent, colorants, moisturizer, thickening agent, preservative, filler, keratolytic agent, protectant agent, vasoconstrictor agent, astringent agent, local anesthetic agent, analgesic/anesthetic/antipruritic agents, and wound healing agent.

Form, Application, and Treatment. The compositions can be in the form of a solid soap; a thick or highly viscous cream; a thin, runny, or low viscosity cream; or a composition of viscosity in between these extremes. The composition can be in the form of a backpacker's or hiker's kit, such as a tube of the treatment material and separate wipes, e.g., alcohol, aqueous, or other liquid-type wipes. Further details of the form are provided below as they relate to the implementation of the granular materials. The solid soap can include the ingredients described herein, including the counterirritant, the granules and the surfactants. Scrubbing the affected area with the soap and a fluid, e.g., water, rubbing alcohol, or other suitable solvent, results in the granules abrading the skin, the counterirritant providing a comforting sensation, and the surfactants forming a complex with the urushiol. Subsequently running water, rubbing alcohol or other suitable solvent over the skin then removes the urushiol from the skin. This treatment can be repeated multiple times over a short time or over a number of hours or days. Generally, the treatment should be repeated if there is itching of the skin.

A thick or highly viscous or granular cream can include the ingredients described herein, including the counterirritant, the granules and the surfactants. By spreading the cream over the area in the presence or absence of a fluid, e.g., water, rubbing alcohol or other suitable solvent, and then scrubbing the area results in the granules abrading the skin, the counterirritant providing a comforting sensation, and the surfactants forming a complex with the urushiol. Subsequently running water, rubbing alcohol or other suitable solvent over the skin then removes the urushiol from the skin. Again, this treatment can be immediately repeated if there is continued itching, or later if an itching sensation develops. The thick or viscous cream can be applied with a cloth or pad, in addition to simply using one's hands. If the cloth or pad is rough, the granules are optional because the rough cloth or pad accomplishes the abrasion caused by the granules.

A thin, runny low viscosity cream or fluid can include the ingredients described herein, including the counterirritant, the granules and the surfactants. By first applying the cream or fluid to the effected area and then scrubbing results in the granules abrading the skin, the counterirritant providing a comforting sensation, and the surfactants forming a complex with the urushiol. In addition to merely using one's hand, the scrubbing can be accomplished by using, for example, a pad or cloth. The pad or cloth can be rough or smooth. If using a rough pad or cloth, the granules are optional because the rough pad or cloth causes the abrasion caused by the granules.

Surfactants (Nonionic Surfactants, Anionic Surfactants)

Surfactants are compounds used to emulsify and solubilize oils, greases and other substances. In the compositions described herein, their primary use is to solubilize the urushiol so that it can be removed from the skin. The surfactants can be a variety of ionic surfactants that have sufficient charge and/or length to allow the surfactant to interact with the urushiol. For example, the following anionic surfactants may be used: Sodium Cocoyl Sarcosinate, Potassium lauryl sacrosinate (Potassium N-Lauroyl, Methyl glycinate), having Formula VI Formula VI Anionic surfactants or detergents include Cocyl Sarcosine, Lauroyl Sarcosine, Myristoyl Sarcosine, Oleoyl Sarcosine, Stearoyal Sarcosine, Sodium Cocoyl Sarcosinate, Sodium Lauroyl Sarcosinate, Sodium Myristoyl Sarcosinate, Ammonium Cocoyl Sarcosinate, and Ammonium Lauroyl Sarcosinate, Ammonium Lauryl Sulfate, Disodium Laureth Sulfosuccinate, Potassium Cocoyl Glycinate, Sodium Cocoyl Isethionate, Sodium Lauryl Sulfate, Sodium Methyl Cocoyl Taurate, Sodium Stearoyl Lactylate, Sodium Cocoyl Glutamate, Sodium Isostearoyl Lactylate, Sodium Lauroyl Sarcosinate, Sodium Lauroyl Glutamate, Sodium Lauroyl Lactylate, Sodium Methyl Cocoyl Taurate, TEA-Lauryl Sulfate, TEA-Cocoyl Glutamate, a mixture of Coconut acid/Arginine/Potassium, a mixture of Sodium Cocoyl Glutamate and Disodium cocoyl glutamate, and a mixture of Sodium Stearoyl Glutamate and Sodium cocoyl glutamate, ammonium laureth sulphate, ammonium lauryl sulfate, dea lauryl sulfate, sodium laureth sulfate, sodium myreth sulfate, sodium lauryl sulfate, tea lauryl sulfate, sodium C14-16 olefin sulfonate, sodium xylenesulfonate, and Sodium Laureth Sulfate (SLES).

Other surfactants that can be used are ethoxylates, such as octyl phenol ethoxylates, Lauryl Alcohol Ethoxylate, Ceto-Stearyl Alcohol Ethoxylate, Cetyl Alcohol Ethoxylate, Stearyl Alcohol Ethoxylate, Tridecyl Alcohol Ethoxylate, Oley Alcohol Ethoxylate, Myristyl Alcohol Ethoxylate, Decyl Alcohol Ethoxylate, Oley-Cetyl Alcohol Ethoxylate, Nonyl Phenol Ethoxylate, Octyl Phenol Ethoxylate, Dodecyl Phenol Ethoxylate, Stearic Acid Ethoxylate, Lauric Acid Ethoxylate, Oleic Acid Ethoxylate, Palmatic Acid Ethoxylate, Butyric Acid Ethoxylate, Castor Oil Ethoxylate, Polyethylene Glycol, and alkyl phenol ethoxylates, such as nonoxynol 12, nonoxynol 30, nonoxynol 4, nonoxynol 6, nonoxynol 9, octoxynol 10, and octoxynol 12. Others are Cocyl Sarcosine, Lauroyl Sarcosine, Myristoyl Sarcosine, Oleoyl Sarcosine, Stearoyal Sarcosine, Sodium Cocoyl Sarcosinate, Sodium Lauroyl Sarcosinate, Sodium Myristoyl Sarcosinate, Ammonium Cocoyl Sarcosinate, and Ammonium Lauroyl Sarcosinate.

It has been said that alkylphenol ethoxylates and alkylphenol are the rubric of a number of phenol ethoxylates and phenol compounds. Nonylphenol ethoxylates are alkylphenolethoxylates with an alkyl chain consisting of nine carbon atoms. Alkylphenol ethoxylates are so-called nonionic surfactants (tensides). Quantitatively, they represent one of the most used groups of tensides in the world. About 80% of the total consumption is made up by nonylphenol ethoxylates which are alkylphenol ethoxylates with an alkyl chain consisting of nine carbon atoms. Octylphenol ethoxylates, which are also used as surfactants, represent a very small part of the total consumption. As the use of nonylphenol ethoxylates is predominant, this name will be used in the following. The chemical structure of nonylphenol ethoxylates consists of a fat-loving (lipophilic) and a water-loving (hydrophilic) part. As it appears from the below FIGURE, these substances are composed by a phenol structure to which can bee bound one (or two) alkyl chains with a chain length of usually nine carbon atoms (nonylphenol ethoxylates), more rarely by eight carbon atoms (octylphenol ethoxylates). The phenol structure and the alkyl chain constitute the lipophilic part of the substance. A chain of ethoxylate groups has also been bound to the phenol structure. The length of this ethoxylate chain may vary much between various types of alkylphenol ethoxylates. The ethoxylate chain constitutes the hydrophilic part of the substance.

Because of their structure nonylphenol ethoxylates are able to reduce the surface tension between two phases, e.g. air/water, oil/water or water/biological membranes. This is the property which causes the extensive use of the substances and as used herein provides a means to remove the urushiol from the skin. The surface active properties of the nonylphenol ethoxylates are used in a large number of products, such as detergents and cleaning materials, insulants, pesticides, paint and lacquer as well as plastic. In pesticides nonylphenol ethoxylates are used as "carriers" of the mixture of active substances which implies that they partly dissolve the active substances in the pesticides, partly increase the absorption of these substances in the target organism. The increased absorption implies that the quantity of active substances can be reduced without modifying their effect.

Considering just one of these ethoxylates, nonylphenol ethoxylate has a molecular formula of $C_9H_{19}C_6H_4(OCH_2CH_2)nOH$ and synonyms for this compound include POE nonyl phenyl ether; polyoxyethylene nonylphenyl ether; nonylphenyl polyethyleneglycol ether, nonionic; ethoxylated nonylphenol; macrogol nonylphenyl ether; and polyethylene mono(nonylphenyl)ether glycols. Applications for these nonylphenol ethoxylates include as nonionic surfactants used as emulsifiers and in formulating emulsifier blends. They also may be used as a wetting agents, dispersants, stabilizers, sanitizers and defoaming agents. The end applications for these ethoxylates include agrochemical emulsifers, industrial cleaners, metal cleaners, textiles, paper de-inking, drilling products and detergents. They also may be used as an intermediate for the synthesis of anionic surfactants.

Some examples of various nonylphenol ethoxylates and their physical characteristics are provided below. Using their physical characteristics described below, one of skill in the art can use the data as a guide, for example, to select the suitable ethoxylates to tailor the physical characteristics of the composition.

The physical and chemical properties for 10 mol nonylphenol ethoxylate are as follows: physical state, white paste; melting point, 1° C.; specific gravity, 1.06; solubility in water, Soluble (Soluble in methanol, Xylene. Insoluble in Kerosene); pH, 6.3 (10% sol.); viscosity (CPA), 240 at 25° C.; and stability, stable under ordinary conditions.

The physical and chemical properties for 2 mol nonylphenol ethoxylate are as follows: appearance, clear oily liquid; specific gravity, 1.03±0.010; cloud point, (1% $H_2O$), less than 25° C.; and approximate HLB, 5.7.

The physical and chemical properties for 4 mol nonylphenol ethoxylate are as follows: appearance, clear oily liquid; specific gravity, 1.03±0.010; cloud point (1% $H_2O$), less than 25° C.; and approximately HLB, 9.

The physical and chemical properties for 5 mol nonylphenol ethoxylate are as follows: appearance, clear oily liquid; specific gravity, 1.035±0.010; cloud point, (1% $H_2O$), less than 25° C.; and approximate HLB, 10.

The physical and chemical properties for 6 mol nonylphenol ethoxylate are as follows: appearance, clear oily liquid; specific gravity, 1.04±0.010; cloud point (1% $H_2O$), less than 25° C.; and approximate HLB, 11.

The physical and chemical properties for 8 mol nonylphenol ethoxylate are as follows: appearance, clear oily liquid; specific gravity, 1.06±0.010; cloud point (1% $H_2O$), less than 25° C.; and approximate HLB, 12.

The physical and chemical properties for 10 mol nonylphenol ethoxylate are as follows: appearance, clear oily liquid; specific gravity, 1.065±0.010; pH, 6.3 (10% Sol.); hydroxyl number, 86-91; color, APHA, 30 max; and approximately HLB, 13.

The physical and chemical properties for 12 mol nonylphenol ethoxylate are as follows: appearance, paste; specific gravity, 1.07±0.010; cloud point (1% $H_2O$), 78-83° C.; and approximate HLB, 14.

The physical and chemical properties for 14 mol nonylphenol ethoxylate are as follows: appearance, paste; specific gravity, 1.07±0.010; cloud point (1% $H_2O$), 92-99° C.; and approximately HLB, 15.

The physical and chemical properties for 30 mol nonylphenol ethoxylate are as follows: appearance, solid; specific gravity, 1.08±0.010; cloud point (1% $H_2O$), greater than 100° C.; and approximate HLB, 17.

The physical and chemical properties for 50 mol nonylphenol ethoxylate are as follows: appearance, solid; specific gravity, 1.08±0.010; cloud point (1% $H_2O$), greater than 100° C.; and approximate HLB, 18.

The chemical formula of nonylphenol ethoxylate is illustrated below in Formula VII:

Formula VII

Other anionic surfactants that can be used are the methyl taurate esters, a group of high flash foam mild anionic surfactants useful in all personal care products, and include sodium methyl cocoyl taurate, sodium cocoyl isethionate, and sodium methyl oleyl taurate.

Another surfactant that can be used is Deionic EAB 95, a modified mixed alcohol ethoxylate (DeIONIC EAB-95 from DeFOREST Enterprises, Inc.)

Other ionic surfactants may be selected from one or more of alkyl ammonium salts; bile acids and salts, analogues, and derivatives thereof; fatty acid derivatives of amino acids, oligopeptides, and polypeptides; glyceride derivatives of amino acids, oligopeptides, and polypeptides; acyl lactylates; monoacetylated tartaric acid esters of monoglycerides, monoacetylated tartaric acid esters of diglycerides, diacetylated tartaric acid esters of monoglycerides, diacetylated tartaric acid esters of diglycerides; succinylated monoglycerides; citric acid esters of monoglycerides; citric acid esters of diglycerides; alginate salts; propylene glycol alginate; lecithins and hydrogenated lecithins; lysolecithin and hydrogenated lysolecithins; lysophospholipids and derivatives thereof; phospholipids and derivatives thereof; salts of alkylsulfates; salts of fatty acids; sodium docusate; and mixtures thereof.

Hydrophobic Surfactants

Hydrophobic surfactants may be, for example, one or more of alcohols; polyoxyethylene alkylethers; fatty acids; glycerol fatty acid monoesters; glycerol fatty acid diesters; acetylated glycerol fatty acid monoesters; acetylated glycerol fatty acid diesters, lower alcohol fatty acid esters; polyethylene glycol fatty acid esters; polyethylene glycol glycerol fatty acid esters; polypropylene glycol fatty acid esters; polyoxyethylene glycerides; lactic acid derivatives of monoglycerides; lactic acid derivatives of diglycerides; propylene glycol diglycerides; sorbitan fatty acid esters; polyoxyethylene sorbitan fatty acid esters; polyoxyethylene-polyoxypropylene block copolymers, polyethyleneglycols as esters or ethers, polyethoxylated castor oil; polyethoxylated hydrogenated castor oil, polyethoxylated fatty acid from castor oil or polyethoxylated fatty acid from castor oil or polyethoxylated fatty acid from hydrogenated castor oil.

Nonionic Surfactants

Nonionic surfactants may be, for example, one or more alkylglucosides; alkylmaltosides; alkylthioglucosides; lauryl macrogolglycerides; caprylocaproyl macrogolglycerides, polyoxyethylene alkyl ethers; polyoxyethylene alkylphenols; polyethylene glycol fatty acid esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene sterols, derivatives, and analogues thereof; polyoxyethylene vegetable oils; polyoxyethylene hydrogenated vegetable oils; reaction products of polyols and at least one member of the group consisting of fatty acids, glycerides, vegetable oils, hydrogenated vegetable oils, and sterols; sugar esters, sugar ethers; sucroglycerides; coconut amidopropylamine oxide, alkylglycoside 8 and mixtures thereof.

Another of the surfactants that is of particular interest in the compositions described herein is nonoxynol-9 (nonylphenoxypolyethoxyethanol) available from Triton N101, Sigma, UK. Nonoxynols are used as non-ionic surface active agents, acting as surfactants in numerous cosmetic products and antiseptic preparations. This surfactant functions as a disinfectant is in a variety of products ranging from baby wipes to laundry detergent. It was invented for use as a contraceptive but nonoxynol-9 was reported to help prevent sexually transmitted diseases (STDs) such as chlamydia, gonorrhea, and herpes by killing sperm and cells in the vaginal tract. It is reported to kill the human immuno deficiency virus in the test tube, according to laboratory tests of commercial sexual products. As little as 0.05 percent of nonoxynol-9 in a solution stops HIV from reproducing, while a 1 to 5 percent concentration may kill cells harboring dormant HIV. They have been found to be irritants or sensitisers and their photosensitising effect has been widely recognized. Acting as an irritant in the compositions described herein provides some relief to the itching caused by the urushiol. Formula VIII illustrates the chemical structure of nonoxynol-9:

Formula VIII

Amphoteric Surfactants

Amphoteric surfactants also can be used in the composition. Examples of amphoteric surfactants include disodium cocoamphodipropionate, cocamidopropyl betaine, and a mixture of disodium cocoamphodiacetate a Wound Healing Agent The composition also may include an agent that functions as a wound healing agent. Examples of wound heating agents include allantoin, carbamide peroxide in anhydrous glycerin, water soluble chlorophyllins, and hydrogen peroxide in aqueous solution.

Analgesic, Anesthetic, and Antipruritic Agent

The composition also may include analgesic, anesthetic, and antipruritic agents. A local anesthetic agent produces local disappearance of pain, burning, itching, irritation, and/ or discomfort by reversibly blocking nerve conduction when applied to nerve tissue in appropriate concentrations. An antipruritic agent is topically (externally) applied and relieves itching by depressing cutaneous sensory receptors. Such agents include: (a) camphor 0.1 to 3 percent; (b) juniper tar 1 to 5 percent; (c) menthol 0.1 to 1 percent.

Local Anesthetic Agent

The compositions may also include a local anesthetic agent. An analgesic, anesthetic agent may be one or more topically (externally) applied agents that relieve pain by depressing cutaneous sensory receptors. Some suitable local anesthetic agents are described by the US FDA at 21 CFR 346.10 and include the following agents used at the following concentrations: (a) Benzocaine 5 to 20 percent; (b) Benzyl alcohol 1 to 4 percent; (c) Dibucaine 0.25 to 1 percent; (d) Dibucaine hydrochloride 0.25 to 1 percent; (e) Dyclonine hydrochloride 0.5 to 1 percent; (f) lidocaine 2 to 5 percent; (g) Pramoxine hydrochloride 1 percent; (h) Tetracaine 0.5 to 1 percent; and (i) Tetracaine hydrochloride 0.5 to 1 percent.

Astringent Agent

The composition may also include an astringent agent. An astringent agent is applied topically (externally) to the skin or mucous membranes for a local and limited protein coagulant effect. Suitable astringent agents include one or more of the following:

(a) calamine, within a concentration range of 5 to 25 percent by weight per dosage unit (based on the zinc oxide content of calamine); (b) witch hazel, 10 to 50 percent; and (c) zinc oxide, within a concentration range of 5 to 25 percent by weight per dosage unit. Other astringent agents recognized by the US FDA include: acetone; alcohol; alum, ammonium; alum, potassium; aluminum chlorhydroxy complex; aromatics; benzalkonium chloride; benzethonium chloride; benzocaine; benzoic acid; boric acid; calcium acetate; camphor gum; clove oil; colloidal oatmeal; cresol; cupric sulfate; eucalyptus oil; eugenol; ferric subsulfate (Monsel's Solution); honey; isopropyl alcohol; menthol; methyl salicylate; oxyquinoline sulfate; P-t-butyl-m-cresol; peppermint oil; phenol; polyoxyethylene laurate; potassium ferrocyanide; sage oil; silver nitrate; sodium borate; sodium diacetate; talc; tannic acid glycerite; thymol; topical starch; zinc chloride; zinc oxide; zinc phenolsulfonate; zinc stearate; and zinc sulfate.

Examples of other astringent agents include: (a) aluminum acetate, (b) aluminum sulfate, and (c) witch hazel. These agents are regulated by the US FDA as skin protectant drug products at 21 CFR Part 347. To comply with these FDA regulations, these astringent agents should be used at the following concentrations for each ingredient: (a) aluminum acetate, 0.13 to 0.5 percent in the resulting solution to be used by the consumer; (b) aluminum sulfate, 46 to 63 percent (the concentration is based on the anhydrous equivalent); and (c) witch hazel. Products containing aluminum acetate are labeled as follows: For temporary relief of minor skin irritations due to poison ivy, poison oak, poison sumac, and insect bites.

Vasoconstrictor Agent

The composition also may include a vasoconstrictor agent, an agent that causes temporary constriction of blood vessels. Suitable vasoconstrictor agents include one or more of the following: (a) ephedrine sulfate 0.1 to 1.25 percent; (b) epinephrine 0.005 to 0.01 percent; (c) epinephrine hydrochloride 0.005 to 0.01 percent; and (d) phenylephrine hydrochloride 0.25 percent.

Protectant Agent

The composition also may include a protectant agent that provides a physical barrier, forming a protective coating over skin or mucous membranes. Examples of protectant agents that may be used as a sole protectant include: (1) aluminum hydroxide gel; (2) cocoa butter; and (3) glycerin in a 20- to 45-percent (weight/weight) aqueous solution so that the final product contains not less than 10 and not more than 45 percent glycerin (weight/weight); (4) hard fat; (5) kaolin; (6) lanolin; (7) mineral oil; (8) petrolatum; (9) topical starch; and (10) white petrolatum.

Examples of protectant agents that may be used in combination with other protectants include: (1) calamine not to exceed 25 percent by weight per dosage unit (based on the zinc oxide content of calamine); (2) cod liver oil, provided that the product is labeled so that the amount of the product that is used in a 24-hour period represents a quantity that provides 10,000 U.S.P. units of vitamin A and 400 U.S.P. units of cholecalciferol; (3) shark liver oil, provided that the product is labeled so that the amount of the product that is used in a 24-hour period represents a quantity that provides 10,000 U.S.P. units of vitamin A and 400 U.S.P. units of cholecalciferol; and (4) zinc oxide not to exceed 25 percent by weight per dosage unit.

Keratolytic Agent

The composition also may include a keratolytic agent. The agents cause desquamation (loosening) and debridement or sloughing of the surface cells of the epidermis. Such agents include: (a) alcloxa 0.2 to 2 percent and (b) resorcinol 1 to 3 percent.

Granular Material

The composition can include granular material or similar agents that function as a roughening means to roughen, penetrate, or scuff the skin and otherwise help the surfactants penetrate to the usushiol. The sizes of the granular materials can vary within the product applied to the skin. The granular means include, for example, one or more of granules, beads, microspheres, grit, and pumice and can be made of, for example, one or more of a polymer, sand, glass, and jojoba beads. The polymer may be, for example, one or more of a polyethylene, a polypropylene, and a polystyrene, or any other suitable polymer. Other roughening means also can be used instead of or along with the granular materials. For example, a scrub pad can be used as a roughening means by placing the composition on the skin and/or scrub pad and rubbing the afflicted area with the scrub pad. The composition can be used alone or with the addition of water. After rubbing the afflicted area for a brief period, the individual washes the afflicted area with water, or other liquid-based or liquid-containing means, to partially or completely remove the composition and urushiol. In place of a scrub pad or granular material, a cloth, pad, brush, or other roughening means may be used.

The granular materials can be porous and in the pores can include one or more of surfactants, therapeutic agents (e.g., antibiotics and antifungals), fluids, and solvents. These materials are released into the skin during the scrubbing of the effected area. In so doing, they form a complex with the urushiol (i.e., surfactant), treat the area (therapeutic agent to prevent infections), and/or aid in removing the complex (i.e., fluid such as water). These materials can be filled into the pores by, for example, soaking or spraying the material onto the granules.

For example, as the granules should be large enough to be effective and it has been recommended that granules in the range of 5 to 50 microns are suitable, although larger granules also will be effective in many circumstances.

Counter-Irritants

Counter-irritants are externally applied agents that cause a reversible, transient, mild inflammation or irritation of the skin to relieve pain or itching beneath the site of application. While their mechanism of action is not completely known, it is believed the sensation they produce on the skin masks the pain or itching occurring more deeply in the skin layers. Some are intended to work by setting up a contrast to the pain and sensations of arthritis (a counter-irritant): for example, by generating heat that might counter arthritis pain by distracting the body's attention, or 'numbing' the response to arthritis. Other reports characterize counter-irritants as inducing local inflammation for the purpose of relieving inflammation in deeper or adjacent tissues. In other words, they substitute one kind of inflammation for another. These agents do not cure, but make the fundamental condition more tolerable.

Counterirritants are divided into four categories by the FDA as listed below.

1. Irritants that produce redness: turpentine oil, methyl salicylate, strong ammonia solution and ally) isothiocyanate 2. Irritants that produce vasodilation: methyl nicotinate and histamine 3. Irritants that produce a cooling sensation: menthol and camphor 4. Irritants that do not produce redness: capsaicin The counter-irritant is provided in the compositions to provide a pain relief effect. The counter-irritant provides a paradoxical pain-relieving effect by producing less severe pain to counter more intense pain. Counter-irritants generally are topical agents applied near painful or irritated sites to produce a mild local inflammatory reaction. As a result, the deep-seated pain or itching is relieved. The intensity of the response depends on the counter-irritant used, its concentration, and the duration of contact with the skin. The action of counter-irritants in relieving pain is reported to have a strong psychological component achieved through a pleasant or strong aroma.

Almost immediately upon application, a counter-irritant initially provides a feeling of coolness, followed by a sensation of warmth. This is due to the counter-irritant (e.g., menthol) causing blood vessels to dilate. The intensity of the response depends on the concentration and duration of contact with the skin.

Tiger Balm. One suitable counter-irritant to use in the compositions described herein is known as Tiger Balm. Tiger Balm, a nonprescription drug applied to the skin or one or more of its individual ingredients may be used in the compositions described herein. The ingredients in Tiger Balm include Menthol, Camphor, Cajeput oil, Peppermint oil, Clove oil, Petrolatum, and Paraffin.

Capsaicin. Capsaicin is derived from the seeds and membranes of various plants in the Nightshade family. It is the most active ingredient in hot chilli peppers and *capsicum*: it is what makes them 'hot'. Its use for arthritis is basically as a counter-irritant. However, it has also been suggested that it might work by depleting a substance from the nerves that helps transmit pain messages to the brain. One use of capsaicin creams is for arthritis. These creams also are used for several other conditions causing pain on the skin, including nerve pain from diabetes (neuropathy), pain after breast removal (mastectomy), and postherpetic neuralgia (continuing pain after an attack of shingles). Capsaicin creams are also sometimes used for psoriasis where it is used to relieve itching, scaling, redness and soreness from psoriasis. It provides a similar effect in the compositions described herein. Moreover, studies from three trials showed that some capsaicin creams were able to relieve pain and tenderness from osteoarthritis, and perhaps also from rheumatoid arthritis. About half the people trying capsaicin cream do not like0 the heat capsaicin generates, and many find that it is so strong for them that it stings or burns. This sensation is one of the reasons that capsaicin is used in the compositions described herein.

Another counter-irritant is *thuja*, from *Thuja occidentalis* (*Biotae orientalis*), and includes 1% volatile oil including thujone, pinene, caryophyllene; pinipicrin, a bitter principle; flavonoid glycoside, mucilage, tannin, and wax. It also is reported as having as its constituents thujone (60%), fenchone, camphor, sabinene, and pinene. Besides being a counter-irritant, it also has the properties of being an astringent, alternative, anthelmintic, diaphoretic, hemostatic, antipyretic, and emmenagogue. It provides a slightly cold sensation upon application. *Thuja* is also believed to have an antiviral activity. *Thuja*'s active principle, a volatile oil called thujone, is reported to act on the muscles of the uterus and Native Americans drank a tea of the inner bark to promote menstruation. It has a role in the treatment of psoriasis and rheumatism as a counter-irritant, improving local blood supply and easing pain and stiffness.

Another counter-irritant is a composition that includes menthol 7.5%, isopropyl alcohol, water, peppermint, eucalyptus and can be formulated as a spray or a roll-on. This formulation is said to provide a nerve blocking effect, act as an analgesic and counter irritant. Upon application, it provides a soothing cold and then warm feeling that will last from one to five hours depending on the severity of the condition and amount applied. This can be used in compositions described herein.

Mint (*Mentha* spp), peppermint, and spearmint. The oil of peppermint has been reported to be antimicrobial and antiviral against Newcastle disease, herpes simplex, vaccinia, Semliki Forest and West Nile viruses. Menthol is an allergic sensitizer that may cause hives. The menthol in oil of peppermint is an effective local anesthetic. It increases the sensitivity of the receptors in the skin that perceive the sensation of coolness and reduces the sensitivity of the receptors that perceive pain and itching (e.g., form urushiol). Menthol is also a counterirritant, causing the small blood vessels under the skin to dilate, increasing the flow of blood to the area and making the skin feel warm. When applied as part of a skin lotion, the skin feels cool for a few minutes, then warm. Some example of mint or its derivatives and constituents are as follows:

(a) *mentha piperita* (peppermint);
(b) *mentha spicata* (spearmint oil);
(c) *mentha viridis* (spearmint oil);
(d) *melissa officinalis* (balm mint);
(e) menthol (derived from peppermint; it can have the same irritating effect as peppermint on skin (Source: Archives of Dermatologic Research, May 1996, pages 245-248));
(f) menthone (major constituent of peppermint);
(g) menthyl lactate (used as a cooling agent and fragrance in cosmetics; it is a derivative of menthol and is supposed to be less irritating than menthol);
(h) mint (can be a skin irritant and cause contact dermatitis);
(i) *coleus barbatus* (member of the mint family; can be a skin irritant);
(j) cornmint (also known as wild mint; it can be a skin irritant);
(k) spearmint oil (fragrant, volatile oil that can cause skin irritation and allergic reactions);
(i) patchouli (fragrant oil derived from mint; it contains eugenol and can be a skin sensitizer and irritant); and
(m) peppermint (both the oil and the extract can have antimicrobial properties (Source: Journal of Agricultural and Food Chemistry, July 2002, pages 3943-3946), and can also have an irritating, sensitizing effect on skin (Source: Natural Medicines Comprehensive Database, naturaldatabase.com)).

Another formulation that can be used as a counter-irritant in the compositions described herein is known as dentilinimentum aconiti compositum N.F. This formulation contains 36 percent menthol and 13.5 percent chloroform in tincture of aconite. It is described as being a powerful counter-irritant and local anesthetic used in neuralgic conditions of the gums and in toothaches. A similar formulation contains 2.2 percent each of menthol and iodine and 16.5 percent chloroform dissolved in tincture of aconite. It is used for similar properties to the above but is less actively counter-irritant but more antiseptic.

Another counter-irritant that may be used is cajuput Oil (Dose: 0-06 to 0-2 ml. (1 to 3 minims). This counter-irritant is a colourless, yellow, or green oil with an agreeable camphoraceous odour and a bitter, aromatic, camphoraceous taste, obtained by distillation from the fresh leaves and twigs of certain species of *Melaleuca* such as *M. leucadendron* and *M. minor* (Myrtaccac). It contains 50 to 65% w/w of cineole. Wt per ml. 0-910 g. to 0-923 g. Soluble 1 in 2 of alcohol (80%), becoming less soluble with age; miscible with alcohol (90%).

Cajuput oil is used externally as a stimulant and mild counter-irritant in rheumatism. In the compositions described herein, cajuput oil, like the other counter-irritants, provides a sensation that relieves the itching caused by the urushiol. It is described in various Pharmacopeias, including India, Spain, and Switzerland.

Another counter-irritant that may be used in the compositions described herein is Nutmeg Oil (01. Myrist.; Myristica Oil; Essence de Muscade; Atherisches Muskatol). Dose: 0-6 to 0-2 ml. (1 to 3 minims). It is a volatile oil obtained by distillation from nutmeg. Physically, it is a colorless or pale yellow liquid with an odor and taste of nutmeg. It is scarcely distinguishable from volatile oil of mace and frequently no commercial distinction is made between the two. Wt per ml. 0-860 to 0-895 g (West Indian oil) and 0-885 to 0-922 g. (East Indian oil). West Indian oil is soluble 1 in 4 of alcohol (90%), East Indian 1 in 3. Nutmeg Oil is known to be a mild counter-irritant and is sometimes used in liniments and hair lotions. Sp. Myrist. (B.P.C. 1949). Spirit of Nutmeg. Oil of nutmeg 10 ml., alcohol (90%) to 100 ml. Dose: 0-3 to 1-2 ml. (5 to 20 minims). Terpeneless Oil of Nutmeg (B.P.C. 1934). 01. Myrist. Deterpenat. Nutmeg oil concentrated in vacuo until reduced to about one-fifth of its volume. 1 fl. oz. Is equivalent in flavour to about 5 fl. oz. of natural oil. It is described in various Pharmacopeias, including Belgium, Germany, India, Switzerland, and the U.S.

Another counter-irritant is clove oil (B.P.) (01. Caryoph.; Esence de Girofle; Nelkenol; Esencia de clavo) Dose: 0-06 to 0-2 ml. (1 to 3 minims). Physically, it is a colorless or pale yellow liquid with the characteristic odor and taste of clove, obtained by distillation from clove. It darkens with age and on exposure to light. It contains 85 to 90% v/v of eugenol. Wt per ml. 1-041 to 1-054 g; soluble 1 in 2 of alcohol (70%); miscible with alcohol (90%) and with ether. Clove oil is applied externally as a rubefacient and counter-irritant. A liniment containing 1 part of clove oil and 2 parts of olive oil has been used to relieve pain in neuralgia. It is described in various Pharmacopeias including Chile, China, Cz., Egypt, France, Germany, Hungary, India, Japan, Jug., Mexico, Spain, Switzerland, and U.S.

Another counter-irritant is spiritus sinapis NF (Spirit of Mustard [Sp. Sinap.]). This counter-irritant contains 2 percent of volatile oil of mustard in alcohol and is known to be used as a counter-irritant.

Another counter-irritant is thyme oil (B.P.C. 1949) (01. Thym.; Esencia de tomillo) Dose: 0-06 to 0-3 ml. (1 to 5 minims). Physically, it is a yellow or dark, reddish-brown liquid with a strong pleasant odour and a biting, persistent, cooling taste, obtained by distillation from the leaves and flowering tops of *Thymus vulgaris* and other species of *Thymus* and of species of *Origanum* (Labiatae). It contains not less than 40% v/v of phenols (thymol and carvacrol). Wt per ml. 0-900 to 0-955 g; soluble 1 in 2 of alcohol (80%). Thyme oil has antiseptic, antispasmodic, and carminative properties and externally it has been employed as a counter-irritant. It is described in various Pharmacopeias including Chil., Dan., Fr., Ger., Hung., Jug., Mex., Nor., Pol., Span., and Swiss (all from *T. vulgaris* only); and Jap. (From *T. vulgaris* and other species of *Thymus*). Also in U.S.N.F. (from *T. vulgaris* and other species of *Thymus*).

Another counter-irritant is allantoin. Allantoin is derived from the comfrey root. It is a white, odorless, crystalline powder that is soluble in water and alcohol. It has been characterized as a counter irritant that helps alleviate the irritating effects of soap, surfactants, oils, acidic and alkaline ingredients. It also is reported to hasten the healing processes of the body, helping the skin to help itself. In texts such as the Merck Index, British Pharmaceutical Codex and the United States Dispensatory it has also been termed a cell proliferant, chemical debrider and epithelization stimulant. It has been said that allantoin can clean away necrotic tissue, speeding the growth of new healthy tissue. The US FDA has only recognized allantoin as a skin protectant, not as a wound healing agent. As a skin protectant, allantoin has long been known to enhance creams and lotions. While allantoin can be used in OTC products (cosmeceuticals) and statements made about its properties, when added to a cosmetic product and no claims are made, the product remains a cosmetic. It is recommended to use it at a rate of 0.5-2.0% w/w. Small concentrations can be added to the water phase, to incorporate more than 0.5% into an emulsion, add during the cooling phase once the temperature has dropped below 50° C./122° F. Its chemical name is glyoxyl-diureide, has a molecular weight of 158.12, a melting range of 225° C., and a solubility in water of 0.5% at 25° C.

The U.S. FDA has classified Allantoin as a Category I (safe and effective) active ingredient skin protectant. The FDA's Tentative Final Monograph on skin protectant drug products for Over-The-Counter (OTC) human use was published in the Federal Register (Volume 48, No. 32, pp. 6820-33 and Volume 55, No. 11, pp. 25240-81). Based on the wide use and clinical acceptance of Allantoin, as well as published reports in the literature, the FDA approved the following statements for non-prescription, drug products containing Allantoin at 0.5% to 2.0%:

1. For the temporary protection of minor cuts, scrapes, burns and sunburn.

2. Helps prevent and temporarily protects chafed, chapped, cracked, or wind-burned skin and lips.

3. Relieves dryness and softens cold sores and fever blisters.

4. Helps treat and prevent diaper rash. Protects chafed skin/minor skin irritation due to/associated with diaper rash and helps protect from/seal out wetness.

A less detailed list of additional counter-irritants that can be used in the compositions described herein includes:

(a) mace (*myristica fragrans*; mace butter is reported as being employed as a mild counter-irritant and used in hair lotions and plasters);

(b) black pepper extract and oil (used topically as a counter-irritant, but that means it can cause significant skin irritation (Source: Natural Medicines Comprehensive Database, naturaldatabase.com));

(c) calamine (a preparation of zinc carbonate, colored with ferric oxide (a form of rust); zinc carbonate is considered a counter-irritant and is used to reduce itching);

(d) Szechuan peppercorn (from a plant native to the Szechuan Province in China; it grows on trees, and so differs from black pepper, which grows on climbing vines; is known for the "numbing" sensation it produces on the tongue and is considered a counter-irritant);

(e) camphor (an aromatic substance obtained from the wood of a southeast Asian tree, *Cinnamomum camphora*, or manufactured synthetically; when applied to the skin it produces a cooling effect and dilates blood vessels, which can cause skin irritation and dermatitis with repeated use (Sources: British Journal of Dermatology, November 2000, pages 923-929; and Clinical Toxicology, December 1981, pages 1485-1498));

(f) *capsicum* (a large group of plants consisting primarily of the pepper family, including chili peppers and paprika; used as counter-irritants to relieve muscle aches);

(g) eucalyptus extract and oil (can have antibacterial, antifungal, and antiviral properties on the skin (Source: Skin Pharmacology and Applied Skin Physiology, January-February 2000, pages 60-64); can also be a skin irritant, particularly on abraded skin (Sources: Clinical Experimental Dermatology, March 1995, pages 143-145; and alternativedr.com/conditions/ConsHerbs/Eucalyptusch.html));

(h) menthyl lactate (used as a cooling agent and fragrance in cosmetics; it is a derivative of menthol and is supposed to be less irritating than menthol);

(i) eucalyptus extract (can have antibacterial, antifungal, and antiviral properties on the skin (Source: Skin Pharmacology and Applied Skin Physiology, January-February 2000, pages 60-64); can also be a skin irritant, particularly on abraded skin (Sources: Clinical Experimental Dermatology, March 1995, pages 143-145); may be derived from the major constituent in eucalyptus leaves is a volatile oil known as eucalyptol (1,8-cineol)); and alternativedr.com/conditions/ConsHerbs/Eucalyptusch.html));

(j) methyl salicylate (a counter irritant used in liniments; the primary ester in the flavour "Oil of wintergreen"; causes a mild irritating action on the skin and therefore acts as a counter-irritant);

(k) chloral hydrate;

(l) 3-1-menthoxy propane-1,2-diol;

(m) N-substituted-p-menthane-3-carboxamides; and (n) acyclic carboxamides.

For example, the following counter-irritants and their recommended amounts are as follows: camphor (greater than 3 to 11 percent), hydrastis, menthol (1.25 to 16 percent), and turpentine oil (rectified) (6 to 50 percent).

Finally, the counter-irritants may be known as skin sensates and are used herein interchangeably. Sensates and counter-irritants may be present at a level of from about 0.01% to about 20%, typically from about 0.1% to about 10%, and particularly from about 0.2% to about 5%, and even more particularly, at less than 1%. The level is selected to provide the desired level of consumer perceived sensation and can be modified as desired. Suitable sensate technologies include menthol, eucalyptus, 3-1-menthoxy propane-1,2-diol, N-substituted-p-menthane-3-carboxamides and acyclic carboxamides, as well as the other counter-irritants described above.

3-1-menthoxy propane 1,2-diol is fully described in detail in U.S. Pat. No. 4,459,425, issued Jul. 10, 1984 to Amano et. al, incorporated herein by reference in its entirety. This volatile aromatic is commercially available, being sold by Takasago Perfumery Co., Ltd., Tokyo, Japan.

The N-substituted-p-menthane-3-carboxamides are fully described in U.S. Pat. No. 4,136,163 to Watson et al., issued Jan. 23, 1979 incorporated herein by reference in its entirety. The most preferred volatile aromatic of this class is N-ethyl-p-menthane-3-carboxamide which is commercially available as WS-3 from Wilkinson Sword Limited.

Useful acyclic carboxamides are fully described in U.S. Pat. No. 4,230,688 to Rowsell et al., issued Oct. 28, 1980 incorporated herein by reference in its entirety. The most preferred volatile aromatic of this class is N,2,3-trimethyl-2-isopropylbutanamide which is commercially available as WS-23 from Wilkinson Sword Limited.

Fillers

Any suitable filler as is known in the art may be used in the compositions.

Preservatives

Any suitable preservative as is known in the art may be used in the compositions.

Thickening Agents

Any suitable thickening agent as is known in the art may be used in the compositions. For example, suspending and thickening agents typically include waxes, silica gels, gums, clays, fumed silica, fatty acid soaps, and various hydrocarbon gels. Hydrocarbon gels comprising di-block, tri-block, multi-block and/or radial or star block copolymers are used in the art as gelling agents or suspending and dispersing agents. See U.S. Pat. No. 5,756,082, WO 98/42298, and EP 0 497 144 B1, the disclosures of which are hereby incorporated by reference. Copolymers of this type are known in the art to have advantageous properties when used as a suspension agent for various solids and liquids. See WO 98/38981, the disclosure of which is hereby incorporated by reference. Other thickening agents, as disclosed in U.S. Pat. No. 6,183,766, the contents of which are incorporated herein by reference, include one or more of polyacrylates; fumed silica, natural and synthetic waxes, crystalline hydroxy-containing waxes, alkyl silicone waxes; aluminium silicate; lanolin derivatives; higher fatty alcohols; polyethylenecopolymers; narogel; polyammonium stearate; sucrose esters; hydrophobic clays; petrolatum; hydrotalcites; and mixtures thereof. Other thickeners include sodium alginate, xanthan gum, quince seed extract, tragacanth gum, starch, hydroxyethyl cellulose, methyl cellulose, carboxymethyl cellulose, hydroxy propylmethyl cellulose, polyvinylpyrrolidone, polyvinylalcohol, guar gum, hydroxypropyl guar gum, soluble starch, cationic celluloses, cationic guars, carboxyvinyl polymers, polyvinylpyrrolidone, polyvinyl alcohol polyacrylic acid polymers, polymethacrylic acid polymers, polyvinyl acetate polymers, polyvinyl chloride polymers, polyvinylidene chloride polymers, aluminium silicates, bentonites, mixtures of polyethylene glycol and polyethylene glycol stearate or distearate, hydrophobically modified celluloses and mixtures thereof. The thickener may be present at a concentration of from about 0.1% to about 5%, or up to 15% for some formulations depending on the need.

Moisturizers

Any suitable moisturizer as is known in the art may be used in the compositions. For example, as disclosed in U.S. Pat. No. 6,183,766, the contents of which are incorporated herein by reference, lipophilic moisturizing agents include petrolatum, mineral oil, micro-crystalline waxes, polyalkenes, paraffin, cerasin, ozokerite, polyethylene, perhydrosqualene, dimethicones, cyclomethicones, alkyl siloxanes, polymethylsiloxanes, methylphenylpolysiloxanes, hydroxylated milk glyceride, castor oil, soy bean oil, maleated soy bean oil, safflower oil, cotton seed oil, corn oil, walnut oil, peanut oil, olive oil, cod liver oil, almond oil, avocado oil, palm oil, sesame oil, liquid sucrose octaesters, blends of liquid sucrose octaesters and solid polyol polyesters, lanolin oil, lanolin wax, lanolin alcohol, lanolin fatty acid, isopropyl lanolate, acetylated lanolin, acetylated lanolin alcohols, lanolin alcohol linoleate, lanolin alcohol riconoleate, beeswax, beeswax derivatives, spermaceti, myristyl myristate, stearyl stearate, carnauba and candelilla waxes, cholesterol, cholesterol fatty acid esters and homologs thereof, lecithin and derivatives, Sphingo lipids, ceramides, glycosphingo lipids and homologs thereof, and mixtures thereof.

Colorants

Any suitable colorant as is known in the art may be used in the compositions.

Emulsifiers

Any suitable emulsifier as is known in the art may be used in the compositions. For example, lanolin and lanolin derivatives may be used as emulsifiers, stabilizers, emollients, moisturizers and absorption bases. They have been used in applications such as creams, lotions, liquid make-up and general purpose cosmetics. Examples of lanolins and derivatives include: anhydrous lanolin USP, polysorbate 80 and cetyl acetate and acetylated lanolin alcohol, cetyl acetate and acetylated lanolin alcohol, lanolin alcohol, PPG-12-PEG-50 lanolin, PPG-12-PEG-65 lanolin, hydroxylated lanolin; PEG 60 lanolin; PEG 75 lanolin, PEG 75 lanolin and water, mineral oil/lanolin alcohol, acetylated lanolin, lanolin oil. In formulating the composition, the emulsifying agent may be made up of emulsifying surfactants in which at least one emulsifying surfactant has an HLB value below 12 and at least one emulsifying surfactant has an HLB value of 12 or above.

Emulsifiers and other ingredients may be used to provide a viscosity suitable to the desired use: For example, if the composition is in the form of an emulsion and more especially in the form of a W/O emulsion, especially in the form of a fluid emulsion, i.e., an emulsion having a viscosity ranging from 60 to 600 cP (60 to 600 mPa·s) and better still from 80 to 250 cP (80 to 250 mPa·s), the viscosity being measured using a Metier RM 180 viscometer (Rheomat) with an M2 spindle, at 25° C. and at a speed of 200 rpm. A fairly fluid emulsion is thus obtained, which is very pleasant to use since it spreads easily.

Wetting Agents

Any suitable wetting agent as is known in the art may be used in the compositions.

Detergents

Any suitable detergent as is known in the art may be used in the compositions.

Humectants

Humectants also may be used in the compositions described herein. Humectants function to retain water on the skin surface. Examples of some humectants include polyhydric alcohols selected from the group consisting of ethylene glycol, propylene glycol, dipropylene glycol, butylene glycol, hexylene glycol, polyethylene glycols, glycerin, sorbitol, panthenols, urea, alkoxylated glucose derivatives, such as Glucam (RTM) E-20, hexanetriol, glucose ethers, sodium hyaluronate, soluble chitosan and mixtures thereof. Glycerin may be, for example, "glycerin, USP, 99.5%", which is sold by Dow Chemical, Inc., Emery Industries, Inc. (under the name "Superol 99.5%"), and Procter & Gamble. Another humectant is "DL-panthenol", which is sold by Hoffman-Laroche. Yet another humectant is PEG/PPG 17/6 copolymer (17 moles ethylene oxide/6 moles propylene oxide), preferably that sold by PPG/Mazer Chemicals or Union Carbide, under the names "Macol 450" and "Ucon 75-H-450". Still another humectant is phytantriol, preferably that sold by Roche. Also polyglycerylmethacrylate lubricants having a viscosity at 25° C. of 300,000 to 1,100,000 mPa·s; a specific gravity at 25.degree. C. of 1 to 1.2 g/ml, a pH of 5.0 to 5.5; a bound water content of 33 to 58%; and, a free water content from 5 to 20% may be used. Suitable polyglycerylmethacrylate lubricants are marketed by Guardian Chemical Corporation under the trademark "Lubrajel". The "Lubrajels" identified as "Lubrajel DV", "Lubrajel MS", and "Lubrajel CG" may be used.

Humectants are may be present, if used, in the compositions at concentrations of from about 0.01% to about 15%, particularly from about 0.5% to about 10%, and more particularly at from about 1% to about 6%.

Alkalinizing Agents

Any suitable alkalinizing as is known in the art may be used in the compositions.

Stabilizers

EDTA. ethylenediaminetetraacetic—Abbreviation for ethylenediaminetetraacetic acid. It is a stabilizer used in cosmetics to prevent ingredients in a given formula from binding with trace elements (particularly minerals) that can exist in water and other ingredients to cause unwanted product changes such as texture, odor, and consistency problems. The technical term for this function is a chelating agent. Additional references, each of which is incorporated herein in their entirety by reference, are provided to further describe suitable stabilizers and their characteristics: chem.sis.nlm.nih, gov/chemidplus/detail frame.html?DetailIndex=1 &DetailCount=1; householdproducts.nlm.nih.gov/cgi-bin/household/brands?tbl=chem&id=888; ghp.org.uk/defaultasp?channel id=398&editorial id=6123; and c°smeticsc°p'c°m/learn/dicti°nary'asp?TYPE=FIND.

Antibacterial Agents

Further, as described above, the compositions can include antibacterial agents and antimicrobial agents. Antimicrobial agents suitable for use are described in U.S. Pat. Nos. 5,686,089; 5,681,802, 5,607,980, 4,714,563; 4,163,800; 3,835,057; and 3,152,181; all of which are herein incorporated by reference in their entirety. When incorporated herein the antimicrobial agent is preferably present, if used, at a concentration of from about 0.001% to about 5%, more preferably 0.05% to about 1%, even more preferably from about 0.05% to about 0.5%, and most preferably 0.1% to about 0.5%.

Also useful as antimicrobial agents are the so-called "natural" antibacterial actives, referred to as natural essential oils. These actives derive their names from their natural occurrence in plants. Typical natural essential oil antibacterial actives include oils of anise, lemon, orange, rosemary, wintergreen, thyme, lavender, cloves, hops, tea tree, citronella, wheat, barley, lemongrass, cedar leaf, cedarwood, cinnamon, fleagrass, geranium, sandalwood, violet, cranberry, eucalyptus, vervain, peppermint, gum benzoin, basil, fennel, fir, balsam, menthol, ocmea *origanum, Hydastis carradensis, Berberidaceae daceae, Ratanhiae* and *Curcuma longa*. Also included in this class of natural essential oils are the key chemical components of the plant oils which have been found to provide the antimicrobial benefit. These chemicals include, but are not limited to anethol, catechole, camphene, carvacol, eugenol, eucalyptol, ferulic acid, farnesol, hinokitiol, tropolone, limonene, menthol, methyl salicylate, thymol, terpineol, verbenone, berberine, ratanhiae extract, caryophellene oxide, citronellic acid, curcumin, nerolidol and geraniol.

Additional antimicrobial agents are antibacterial metal salts. This class generally includes salts of metals in groups 3b-7b, 8 and 3a-5a. Specifically included are the salts of aluminum, zirconium, zinc, silver, gold, copper, lanthanum, tin, mercury, bismuth, selenium, strontium, scandium, yttrium, cerium, praseodymium, neodymium, promethium, samarium, europium, gadolinium, terbium, dysprosium, holmium, erbium, thulium, ytterbium, lutetium and mixtures thereof.

Preferred antimicrobial agents include piroctoneolamine (hereinafter Octopirox®) available from Hoechst AG; 2,4,4'-trichloro-2'-hydroxy diphenylether (hereinafter "TCS" or "Triclosan®") available from Ciba-Geigy Corp.; 3,4,4'-trichlorocarbanilide (hereinafter "TCC" or "Triclocarban®") available from Bayer AG; para-chloro-meta-xylenol (hereinafter PCMX) available from Rhone Poulenc; zinc pyrithione (hereinafter "ZPT") available from the Olin Corp.; 1-phenoxypropan-2-ol available from Nippa Laboratories Ltd.; benzalkonium chlorides and/or substituted benzalkonium chlorides such as those available from Lonza under the tradename Barquat®; benzoyl peroxide, erythromycin, tetracycline, clindamycin, azelaic acid, sulfur compounds such as sulfonamides, resorcinol, essential oils and their key ingredients and mixtures thereof. Also useful herein is the antimicrobial compositions described in PCT Applications WO98/55080 and WO98/55081, Baier et al., both published Dec. 10, 1998, both of which are herein incorporated by reference in its entirety.

Antifungal Agents

Also useful in the compositions described herein are antifungal agents. Suitable antifungal agents include, in particular compounds belonging to the imidazole class such as clotrimazole, econazole, ketoconazole, fluconazole, or miconazole or salts thereof, polyene compounds such as amphotericin B, compounds of the allylamine family such as terbinafine, or octopirox. Also useful herein are naftifine, tolnaftate, nystatin, 5-fluorocytosine, griseofulvin, and haloprogin. Mixtures of the above antifungals can also be used. A detailed discussion of antifungals as well as additional examples can be found in Remington's pharmaceutical Sciences, 17th ed. (Alfonso R. Gennaro ed., 1985) pp. 1225-1231, herein incorporated by reference.

When incorporated in the compositions, the antifungal agent may be present at a concentration of from about 0.001% to about 5%, more particularly at 0.05% to about 1%, even more particularly at from about 0.05% to about 0.5%, and still more particularly at 0.1% to about 0.5%.

Approved FDA Ingredient

Finally, the compositions described herein may specifically include an ingredient accepted or approved by the FDA (defined herein as an "approved FDA ingredient") in a monograph or for OTC usage such that the product can be labeled for treatment of poison ivy, poison oak, or poison sumac. The approved FDA ingredients, as defined herein are the following:

(a) for labeling for poison ivy, poison oak, and poison sumac drug products: alcohol, anion and cation exchange resins buffered, Beeswax, Benzethonium chloride, Benzocaine (0.5 to 1.25 percent), Benzocaine Bithionol, Benzyl alcohol, Bismuth subnitrate, Bithionol, Boric acid, Calamine, Camphor, Cetalkonium chloride, Cetyl alcohol, Cyclomethycaine sulfate, Chloral hydrate, Chlorobutanol, Chlorpheniramine maleate, Creosote, Creosote (beechwood), Dexpanthenol, Diperodon hydrochloride, Diphenhydramine hydrochloride, Eucalyptus oil, Eugenol, Ferric chloride, Glycerin, Glyceryl stearate, Glycol salicylate, Hectorite, Hexylresorcinol, Hydrogen peroxide, Impatiens biflora tincture, Iron oxide, Isopropyl alcohol, Isopropyl palmitate, Lanolin, Lead acetate, Lidocaine, Live yeast cell derivative, Menthol, Merbromin, Mercuric chloride, Methapyrilene hydrochloride, Panthenol, Parethoxycaine hydrochloride, Phenol, Phenyltoloxamine dihydrogen citrate, Povidone-vinylacetate copolymers, Pyrilamine maleate, Salicylamide, Salicylic acid, Simethicone, Shark liver oil, Stearyl alcohol, Sulfur, Tannic acid, Thymol, Topical starch, Trolamine, Trolamine salicylate, Turpentine oil, Zirconium oxide, and Zyloxin;

(b) for labeling for fever blister and cold sore treatment: Allyl isothiocyanate, Aspirin, Bismuth sodium tartrate, Camphor (exceeding 3 percent), Capsaicin, *Capsicum, Capsicum* oleoresin, Chloral hydrate, Chlorobutanol, Cyclomethycaine sulfate, Eucalyptus oil, Eugenol, Glycol salicylate, Hexylresorcinol, Histamine dihydrochloride, Menthol (exceeding 1 percent), Methapyrilene hydrochloride, Methyl nicotinate, Methyl salicylate, Pectin, Salicylamide, Strong ammonia solution, Tannic acid, Thymol, Tripelennamine hydrochloride, Trolamine salicylate, Turpentine oil, and Zinc sulfate;

(c) for labeling for insect bite and sting: Alcohol; Alcohol, ethoxylated alkyl; Ammonia solution (strong); Ammonium hydroxide; Benzalkonium chloride; Calamine; Camphor; Ergot fluid extract; Ferric chloride; Menthol; Panthenol; Peppermint oil; Pyrilamine maleate; Sodium borate; Trolamine salicylate; Turpentine oil; Zinc oxide; and Zirconium oxide; Phenol; Beeswax; Bismuth subnitrate; Boric acid; Cetyl alcohol; Glyceryl stearate; Isopropyl palmitate; Live yeast cell derivative; Shark liver oil; and Stearyl alcohol.

(d) for labeling for external analgesic drug products: Chloral hydrate, Chlorobutanol, Cyclomethycaine sulfate, Eugenol, Hexylresorcinol, Methapyrilene hydrochloride, Salicylamide, and Thymol.

While several particular forms of the inventions have been illustrated and described, it will be apparent that various modifications can be made without departing from the spirit and scope of the invention. For example, even if not specifically indicated, any of the ingredients described above can be included in the compositions or excluded from the compositions. Accordingly, it is not intended that the invention be limited, except as by the appended claims.

The invention claimed is:

1. A method for treating a condition caused by the contact of skin with a source of urushiol, the method comprising:
providing a skin drying topical scrub intended to be applied to skin that has been in contact with the source of urushiol to remove the urushiol from the skin, the topical scrub consisting essentially of:
at least one anionic surfactant and at least one nonionic surfactant selected to form a complex with the urushiol such that removal of the surfactants from the skin removes the urushiol with the surfactants and causes a drying of the skin upon which the surfactants are applied;
one or more granular materials configured to roughen skin that has been in contact with urushiol and provide a sensation on the skin that causes at least some relief of the itching caused by the urushiol upon a scrubbing application of the topical scrub; and
one or more counterirritants, whereby the one or more surfactants is used in removing the urushiol from the skin and the one or more counterirritants provide a sensation on the skin to which the topical scrub has been applied;
scrubbing the skin with the topical scrub to cause a roughening abrasion of the skin, penetration of the surfactants into the skin to form a complex with the urushiol, and a contact between the skin and the counterirritants such that the counterirritants provide a sensation to the skin; and
removing the topical scrub from the skin having the rash by applying a fluid to the skin upon which the topical scrub has been applied, whereby removing the topical scrub from the skin removes urushiol from the skin and dries the skin.

2. The method of claim 1, wherein the topical scrub further consists essentially of one or more alkalizing agents, humectants, detergents, wetting agents, antibacterial agents, stabilizers, emulsifiers, antifungal agents, colorants, moisturizers, thickening agents, preservatives, fillers, keratolytic agents, protectant agents, vasoconstrictor agents, astringent agents, local anesthetic agents, analgesic/anesthetic/antipruritic agents, antiviral agents, and wound healing agents.

3. The method of claim 1, wherein the one or more counterirritants comprise one or more of menthol and camphor.

4. The method of claim 1, wherein the one or more granular materials have a diameter greater than 50 microns.

5. The method of claim 1, wherein the granular material comprises one or more of granules, beads, microspheres, grit, pumice, polymer, sand, glass, and jojoba beads.

6. The method of claim 1, wherein the granular materials comprise a pad, cloth or scrubbing means.

7. The method of claim 1, wherein the contact with the urushiol occurred more than 24 hours before the application of the topical scrub.

8. The method of claim 1, wherein the contact with the urushiol occurred more than 72 hours before the application of the topical scrub.

9. The method of claim 1, wherein the topical scrub is applied to a rash formed by the contact with the urushiol.

10. A method of treating a rash caused by contact with urushiol, the method comprising:

providing a skin drying topical scrub in the form of a cream for removing urushiol from skin by using the topical scrub cream to scrub skin that has been in contact with urushiol and dry the skin, the topical scrub cream consisting essentially of:

at least one anionic surfactant and at least one nonionic surfactant selected to form a complex with the urushiol such that removal of the surfactants from the skin removes the urushiol with the surfactants and causes a drying of the skin upon which the surfactants are applied;

one or more granular materials configured to roughen skin that has been in contact with urushiol and provide a sensation on the skin that causes at least some relief of the itching caused by the urushiol upon a scrubbing application of the topical scrub; and one or more counterirritants, whereby the one or more surfactants is used in removing the urushiol from the skin and the one or more counterirritants provide a sensation on the skin to which the topical scrub has been applied scrubbing the skin having a rash with the topical scrub cream to cause a roughening abrasion of the skin, penetration of the surfactants into the roughened skin to form a complex with the urushiol, and a contact between the skin and the counterirritants such that the counterirritants provide a sensation to the skin to cause relief of the itching; and removing the topical scrub cream from the skin having the rash by applying a fluid to the skin upon which the topic scrub has been applied, whereby removing the topical scrub cream from the skin by applying the fluid removes urushiol from the skin and dries the skin.

11. The method of claim 10, wherein the one or more counterirritants comprise one or both of menthol and camphor.

12. The method of claim 10, wherein the one or more granular materials have a diameter greater than 50 microns.

13. The method of claim 10, wherein the topical scrub cream further consists essentially of one or more additional agents selected from the group consisting of antifungal agents, antibiotic agents, and antiviral agents.

14. The method of claim 10, wherein the granular material comprises one or more of granules, beads, microspheres, grit, and pumice.

15. The method of claim 10, wherein the granular material comprises one or more of a polymer, sand, glass, and jojoba beads.

16. The method of claim 15, wherein the polymer comprises one or more of a polyethylene, a polypropylene, and a polystyrene.

17. The method of claim 10, wherein the granular material is porous.

18. The method of claim 10, wherein the granular material is a pad, cloth or other scrubbing means.

19. The method of claim 1, wherein the topical scrub is in the form of a cream.

20. The method of claim 1, further comprising repeating the treatment with the topical scrub if there is an itching of the skin where the rash is present.

* * * * *